United States Patent [19]

Ikimi et al.

[11] Patent Number: 5,399,791
[45] Date of Patent: Mar. 21, 1995

[54] PROCESS FOR PRODUCTION OF CRESOLS

[75] Inventors: Kiyoshi Ikimi; Yoichi Ikeda; Akira Murakami; Kazushige Okamoto; Tooru Tokumaru; Motoo Hazama, all of Oita, Japan

[73] Assignee: Suitomo Chemical Company, Limited, Osaka, Japan

[21] Appl. No.: 202,160

[22] Filed: Feb. 25, 1994

Related U.S. Application Data

[63] Continuation-in-part of Ser. No. 10,837, Jan. 29, 1993, abandoned.

[30] Foreign Application Priority Data

Jan. 31, 1992 [JP] Japan ................................ 4-16136

[51] Int. Cl.⁶ ........................ C07C 37/08; C07C 37/06
[52] U.S. Cl. ........................ 568/798; 568/754; 568/799
[58] Field of Search ................ 568/717, 798, 799, 754

[56] References Cited

U.S. PATENT DOCUMENTS

4,163,863  8/1979  Ikarashi et al. .

FOREIGN PATENT DOCUMENTS

2650416  11/1975  European Pat. Off. .
0077749   4/1983  European Pat. Off. .
52-7130    5/1977  Japan .
58-198468 11/1983  Japan .
59-8246    2/1984  Japan .

OTHER PUBLICATIONS

Chem. Abs., vol. 88, 1978, p. 722 88:190380m Cresols.

*Primary Examiner*—Alan Siegel
*Attorney, Agent, or Firm*—Birch, Stewart, Kolasch & Birch

[57] ABSTRACT

There is disclosed a process for the production of cresols, including the steps of: (a) conducting oxygenation of cymene with oxygen gas or an oxygen-containing gas without any addition of an alkali, thereby obtaining a solution of oxygenation products containing tertiary and primary hydroperoxides of cymene; (b) washing the solution of oxygenation products obtained in step (a) with an aqueous alkali solution at a temperature in the range of from 10° to 95° C.; (c) subjecting the solution of oxygenation products obtained in step (b) to hydrogenation at a temperature in the range of from 60° to 100° C. to decrease the content of primary hydroperoxide in such a manner that the weight ratio of primary hydroperoxide to tertiary hydroperoxide is not greater than 1/25 (w/w); (d) subjecting the solution treated in step (c) to decomposition in the presence of a catalyst; and (e) subjecting the solution treated in step (d) to hydrogenation to obtain cresols.

19 Claims, No Drawings

PROCESS FOR PRODUCTION OF CRESOLS

CROSS REFERENCE TO RELATED APPLICATION

The present application is a continuation-in-part of application Ser. No. 08/010,837, filed Jan. 29, 1993, now abandoned.

FIELD OF THE INVENTION

The present invention relates to a process for the production of cresols.

BACKGROUND OF THE INVENTION

As a process for cresol production, there has been widely known a process in which cymene is oxygenated with oxygen gas and tertiary hydroperoxide of cymene is then decomposed into the desired cresols and acetone.

In this process, however, a primary hydroperoxide of cymene with an oxygenated methyl group is formed as a by-product in the oxygenation, together with the above tertiary hydroperoxide. The primary hydroperoxide is converted into isopropyl-phenol and formaldehyde through its decomposition. This formaldehyde may be condensed with the resulting cresols to form a resin, which will cause a decrease in the yield of cresols in this process.

To solve this problem, a process has been proposed, in which the decomposition of the primary hydroperoxide is stopped halfway to suppress the formation of formaldehyde, so that a yield decrease arising from the by-product can be prevented, and the remaining primary hydroperoxide is then hydrogenated into an alkylbenzene (see, e.g., JP-A 52-57130, JP-B 59-8246, JP-B 1-49248).

In this process, however, a portion of the primary hydroperoxide still decomposes. Therefore there will inevitably occur to a certain degree the side reaction between formaldehyde as the by-product and cresols as the major product, so that a loss of cresol yield will accompany the process. This process is not satisfactory with respect to the yield of cresols.

For the purpose of preventing the formation of formaldehyde, a process has been known, in which a mixture of the tertiary and primary hydroperoxides obtained by the oxygenation is subjected to hydrogenation below 50° C. to decrease the content of primary hydroperoxide (see, e.g., JP-A 58-198468). In this process, a yield decrease arising from the formation of formaldehyde can be suppressed. However, the yield of cresols in this process cannot be satisfactory either. Further, the energy efficiency in the process is poor because the reaction temperature is 50° C. or lower, and it cannot always be said that this process is satisfactory from an industrial point of view.

SUMMARY OF THE INVENTION

Under these circumstances, the present inventors have intensively studied a production process for cresols. As the result, the present invention has been completed with the novel finding that cresols can be obtained in high yield from consumed cymene because a yield decrease arising from the formation of formaldehyde can be prevented and the primary hydroperoxide and other by-products can also be selectively recovered as the raw material cymene.

Thus, the present invention provides a process for the production of cresols, comprising the steps of: (a) conducting oxygenation of cymene with oxygen gas or an oxygen-containing gas without any addition of an alkali, thereby obtaining a solution of oxygenation products containing tertiary and primary hydroperoxides of cymene; (b) washing the solution of oxygenation products obtained in step (a) with an aqueous alkali solution at a temperature in the range of from 10° to 95° C.; (c) subjecting the solution of oxygenation products obtained in step (b) to hydrogenation at a temperature in the range of from 60° to 100° C. to decrease the content of primary hydroperoxide in such a manner that the weight ratio of primary hydroperoxide to tertiary hydroperoxide is not greater than 1/25 (w/w); (d) subjecting the solution treated in step (c) to decomposition in the presence of a catalyst; and (e) subjecting the solution treated in step (d) to hydrogenation to obtain cresols.

DETAILED DESCRIPTION OF THE INVENTION

The following will describe the step of conducting the oxygenation of cymene with oxygen gas or an oxygen-containing gas to obtain a solution of oxygenation products containing tertiary and primary hydroperoxides of cymene.

Examples of the raw material cymene which can be used in this step are in various forms such as o-cymene, m-cymene and p-cymene. Among these cymene isomers, any single isomer can be used solely or mixtures thereof in any ratio can also be used.

This step is performed without any addition of an alkali. When an alkali is added, the decomposition of primary hydroperoxide is enhanced, so that it is mostly oxygenized into the corresponding carboxylic acid, thereby making it difficult to recover the primary hydroperoxide as the raw material cymene and causing a reduction in the degree of conversion into cresol.

In this step, the weight ratio of primary hydroperoxide to tertiary hydroperoxide is preferably adjusted to not less than 10/90 (w/w).

This step can be performed by ordinary oxygenation in liquid phase, and usually attained by bringing cymene in contact with oxygen gas or an oxygen-containing gas such as air. At that time, preferred is direct oxygenation of cymene with oxygen, example of which oxygenation is conducted without any dilution of the raw material cymene.

The oxygenation is usually conducted under normal pressure or under pressure. The pressure of oxygen gas or an oxygen-containing gas is usually in the range of from 0 to 20 kg/cm$^2$ as a gauge pressure.

In this step, an initiator may be added to the reaction system, examples of which are azo compounds such as 2,2'-azobisisobutyronitrile, and peroxides such as benzoyl peroxide and cymene hydroperoxide. The amount of initiator to be used is usually in the range of from 0.01% to 5% by weight, based on the weight of cymene.

The reaction temperature is usually in the range of from 30° to 200° C., preferably 80° to 150° C. After completion of the reaction, a solution of oxygenation products is obtained. The resulting solution of oxygenation products is washed, before its use in the subsequent step, with an aqueous solution of alkali substances such as hydroxides of alkali metals, carbonates of alkali metals, hydroxides of alkaline earth metals or carbonates of alkaline earth metals. The aqueous alkali solution has a concentration of 0.1 to 2.0 wt %, and the weight ratio of the aqueous alkali solution to the solution of oxygenation products is in the range of from 1/5 to 1/15 (w/w). The alkali washing is usually conducted at a temperature in the range of from 10° to 95° C., preferably 50° to 90° C., and more preferably 60° to 90° C. The alkali washing can attain the extraction, into the water phase, of acidic ingredients contained in the solution of oxygenation products, such as formic acid and cresol.

The following will describe the step of subjecting the solution of oxygenation products obtained in the foregoing step to hydrogenation to decrease the content of the primary hydroperoxide.

This step can be performed by ordinary catalytic hydrogenation, and usually attained by introducing hydrogen gas under normal pressure or under pressure in the presence of a catalyst. The pressure of hydrogen gas is usually in the range of from 0 to 20 kg/cm² as a gauge pressure.

Examples of the catalyst which can be used in this step are those composed of a metal such as Pd, Pt, Ni, Ru, Rh or Re. These catalysts can also be used in a supported form on a carrier such as active carbon, titania, zirconia, silica-magnesia, alumina or alumina-magnesia. Preferred are Pd catalysts and Ni catalysts. More preferred are Pd/C, Pd/alumina, Pd/TiO$_2$, Pd/alumina-magnesia, Pd/silica-magnesia and Raney Ni. The amount of catalyst to be used is usually in the range of from 0.001% to 1% by weight, based on the weight of the solution of oxygenation products.

The reaction temperature is in the range of from 60° to 100° C.

By this hydrogenation, the primary hydroperoxide is converted into a compound which will give no more formaldehyde in the subsequent decomposition step, and hence there is no possibility that the yield of cresols may be decreased by the side reaction in the decomposition step. Moreover, by the additional hydrogenation after the decomposition, the compounds produced in the first hydrogenation step of the primary hydroperoxide, as well as the other by-products in the reaction mixture resulted in the decomposition, are converted into the raw material cymene which will be recycled. Thus, the yield of cresols from consumed cymene will finally increase.

In the hydrogenation, the tertiary hydroperoxide can also be reacted, together with the primary hydroperoxide. The reaction rate of the tertiary hydroperoxide is considerably lower than that of the primary hydroperoxide, and the reaction products obtained from the tertiary hydroperoxide by the hydrogenation can be recycled as the raw material, if any; therefore, the hydrogenated tertiary hydroperoxide will not affect the yield of cresols from consumed cymene. It is, however, disadvantageous from an economical point of view that the hydrogenation is conducted to a degree than required. It is usually advantageous from an economical point of view, i.e., the yield of cresols through one pass and the energy efficiency in the process, that the hydrogenation is conducted in such a manner that the weight ratio of primary hydroperoxide to tertiary hydroperoxide is usually decreased to not greater than 1/25 (w/w), preferably not greater than 1/50 (w/w), more preferably not greater than 1/100 (w/w), and that the degree of hydrogenation of tertiary hydroperoxide as the precursor of cresols is 30% or less, preferably 20% or less, more preferably 15% or less. These results of hydrogenation can be attained by adjusting the reaction temperature and pressure for hydrogenation, as well as the kind and mount of catalyst to be used for hydrogenation, to the above prescribed conditions.

In this step, the solution thus treated may be subjected to an analysis such as liquid chromatography to check the degrees of conversion of primary and tertiary hydroperoxides, which also makes it possible to determine the end point of the reaction.

After completion of the reaction, the catalyst is removed, for example, by filtration, and the residue may be used in the subsequent step, if necessary, after subjected to a post-treatment such as alkali washing and concentration.

The following will describe the step of subjecting the solution obtained in the foregoing step to decomposition in the presence of a catalyst.

Examples of the catalyst which can be used in this step are acidic catalysts, sulfur and metal complex catalysts such as Burmah catalyst. Specific examples of the acidic catalyst are inorganic acids such as sulfuric acid, hydrochloric acid, perchloric acid, SO$_2$ and SO$_3$; organic acids such as benzenesulfonic acid, p-toluenesulfonic acid, cresolsulfonic acid and chloroacetic acid; solid acids such as silica-alumina, alumina and strongly acidic ion exchange resin; heteropolyacids such as tungstosilicic acid, tungstophosphoric acid and molybdophosphoric acid. The Burmah catalyst refers to a catalyst of the general formula:

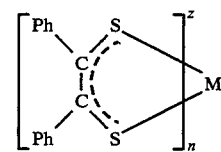

wherein M is Ni, Pd or Fe(II); Ph is a phenyl group which may be optionally substituted with at least one substituent; n is an integer of 1, 2, or 3; z is a formal charge of the complex, selected from 0, −1 and −2. Examples of the Burmah catalyst are bis(dithiobenzil)-nickel, bis(dithiobenzil)palladium and bis(dithiobenzil)iron(II). Preferred are sulfuric acid and cresolsulfonic acid. The mount of catalyst to be used, although it can be determined depending upon the kind of that catalyst, is usually in the range of from about 0.0001% to 1% by weight, based on the weight of the solution obtained after the hydrogenation.

The reaction temperature is usually in the range of from 30° to 150° C., preferably from 60° to 150° C.

In this step, the solution thus treated may be further subjected to an analysis such as liquid chromatography to check the degree of decomposition of hydroperoxides.

By this decomposition, the tertiary hydroperoxide is decomposed into the desired cresols and acetone.

After completion of the reaction, the reaction mixture can be used in the subsequent step without undergoing a particular post-treatment, or if necessary, after subjected to a post-treatment such as filtration and neutralization. The reaction mixture can also be used in the subsequent step after the removal of produced acetone.

The following will describe the step of subjecting the solution thus treated to hydrogenation.

This step can be performed by ordinary catalytic hydrogenation, and usually attained by introducing hydrogen gas in the reaction system under normal pressure or under pressure in the presence of a catalyst. The pressure of hydrogen gas is usually in the range of from 0 to 100 kg/cm² as a gauge pressure.

Examples of the catalyst which can be used in this step are those composed of a metal such as Pd, Cr, Cu, Pt, Ni, Ru, Rh or Re. These catalysts can also be used in a supported form on a carrier such as active carbon, titania, zirconia, silica-magnesia, alumina, alumina-magnesia or strongly acidic ion exchange resin. Preferred are those composed of Pd or Cu—Cr. More preferred are Pd/C, Pd/alumina, Pd/TiO₂, Cu—Cr/C, Cu—Cr/TiO₂ and Pd/strongly acidic ion exchange resin. The amount of catalyst to be used is usually in the range of from 0.001% to 20% by weight, based on the weight of the solution after the decomposition.

In this step, any other catalyst may be allowed to coexist in the reaction system, if necessary. Examples of such a catalyst are the same catalysts as used in the decomposition step. The reaction mixture after the decomposition may be used as it is, without undergoing the removal of the catalyst used in the decomposition step.

The reaction temperature is usually in the range of from 0° to 250° C., preferably 20° to 250° C., and more preferably 60° to 250° C.

After the completion of the reaction, the removal of the catalyst by filtration gives cresols, cymene and acetone, which can be separated and purified, if necessary, by neutralization and then distillation. The portion of cymene obtained by the hydrogenation can be recovered, together with the unreacted portion of cymene, and both can be recycled as the raw material in the process of the present invention.

The process of the present invention can be performed either by a batch method or a continuous method.

The process of the present invention can afford cresols in high yield because not only the primary hydroperoxide but also other by-products are recovered as cymene by two hydrogenation steps, i.e., one after the oxygenation of cymene with oxygen gas or an oxygen-containing gas and the other after the decomposition reaction of tertiary hydroperoxide into cresols.

Accordingly, the formation of formaldehyde from the primary hydroperoxide, hence a yield decrease thereby, is almost negligible.

The process of the present invention has an additional advantage that the resulting cresols can readily be isolated from the by-products.

The present invention will be illustrated by way of the following examples which are not to be construed to limit the scope thereof.

The abbreviations used in the Examples are shown below together with their corresponding chemical structures.

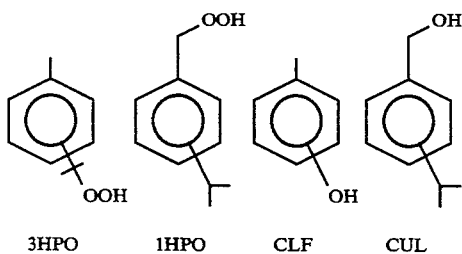

3HPO   1HPO   CLF   CUL

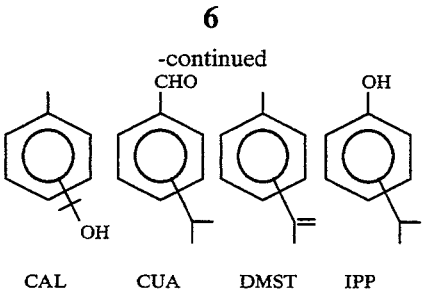

CAL   CUA   DMST   IPP

EXAMPLE 1

I. In a reaction vessel equipped with a stirrer, an air-blowing tube, a thermometer and a condenser, placed are cymene (807.0 g; content, 99.3%) and a cymene solution (78.0 g; cymene content, 82.1%; 3HPO content, 11.2%; and 1HPO content, 0.65%) containing cymene hydroperoxide. The reaction is conducted, while blowing air thereinto, at 120° C. under normal pressure for 5 hours. The reaction mixture is then washed at 70° C. with 1% aqueous sodium hydroxide (90 g) to give 909.2 g of a hydroperoxide mixture-containing oil phase (composition: cymene, 81.9%; 3HPO, 12.1%; 1HPO, 2.2%; CAL, 1.0%; CUL, 0.23%; CUA, 0.20%; CLF, 0.01%; and others, 2.4 %).

II. The hydroperoxide mixture-containing oil phase (909.2 g) obtained in Sec. I. of this Example and 1% palladium-titania catalyst (0.45 g) are placed in a flask. Hydrogenation is conducted with stirring, while blowing hydrogen gas thereinto, at 70° C. under normal pressure for 1 hour. After completion of the reaction, the removal of the catalyst by filtration gives 909.2 g of the reaction mixture (composition: cymene, 81.8%; 3HPO, 11.0%; 1HPO, 0.03%; CAL, 2.4%; CUL, 1.7%; CUA, 0.72%; CLF, 0.01%; and others, 2.2%). The weight ratio of 1HPO to 3HPO in the reaction mixture is 1/370, and the degree of conversion is 98.7% for 1HPO and 8.7% for 3HPO, respectively.

From this reaction mixture, the unreacted portion (699.8 g) of cymene is removed by distillation at 70° C. under a pressure of from 10 to 20 mmHg, 209.3 g of the concentrate is obtained (composition: cymene, 21.0%; 3HPO, 47.8%; 1HPO, 0.13%; CAL, 10.5%; CUL, 7.6%; CUA, 3.1%; CLF, 0.04%; and others, 9.8%).

III. Concentrated sulfuric acid (0.17 g) and acetone (29 g) are placed in a flask, and the mixture is heated to reflux, to which the concentrate (209.3 g) obtained in Sec. II. of this Example is added dropwise under reflux. The reaction mixture is maintained at 65° C. for 0.5 hours. After completion of the reaction, 238.3 g of the solution of decomposition products is obtained (composition: cymene, 18.3%; 3HPO, not found; 1HPO, not found; CAL, 0.88%; CUL, 5.6%; CUA, 2.6%; DMST, 5.1%; CLF, 26.0%; acetone, 26.9%; and others, 14.7%). The yield of cresol from consumed cymene is 59.4%.

IV. In an autoclave made of stainless steel, placed are the solution of decomposition products (238.3 g) obtained in Sec. III. of this Example and 1% palladium-titania catalyst (4.7 g). The reaction is conducted, while introducing hydrogen gas thereinto under a hydrogen gauge pressure of 4 kg/cm², at 75° C. for 2 hours. After completion of the reaction, the catalyst is removed by filtration, and the resulting solution is neutralized by addition of aqueous sodium hydroxide until the water layer has pH 7. From the organic layer obtained, acetone is removed by distillation under normal pressure, and the residue is then distilled under reduced pressure to give 63.0 g of cresol and 82.1 g of cymene. The yield of cresol from consumed cymene is 86%.

EXAMPLE 2

I. In a reaction vessel equipped with a stirrer, an air-blowing tube, a thermometer and a condenser, placed are cymene (820.3 g; content, 99.9%) and a cymene solution (65.4 g; cymene content, 84.06%; 3HPO content, 8.51%; and 1HPO content, 0.47%) containing cymene hydroperoxide. The reaction is conducted, while blowing air thereinto, at 120° C. under normal pressure for 5 hours. After completion of the reaction, 897.2 g of a hydroperoxide mixture-containing oil phase (composition: cymene, 90.0%; 3HPO, 7.6%; 1HPO, 1.3%; CAL, 0.45%; CUL, 0.07%; CUA, 0.09%; CLF, <0.01%; and others, 0.44%) is obtained.

II. The hydroperoxide mixture-containing oil phase (897.2 g) obtained in Sec. I. of this Example and 1% palladium-carbon catalyst (0.45 g) are placed in a flask. Hydrogenation is conducted with stirring, while blowing hydrogen gas thereinto, at 27° C. under normal pressure for 1 hour. After completion of the reaction, the catalyst is removed by filtration, and the reaction mixture is washed with 1% aqueous sodium carbonate (90 g) to give 896.0 g of the reaction mixture (composition: cymene, 90.1%; 3HPO, 6.7%; 1HPO, 0.13%; CAL, 1.4%; CUL, 0.89%; CUA, 0.53%; CLF, 0.01%; and others, 0.18%). The weight ratio of 1HPO to 3HPO in the reaction mixture is 1/52, and the degree of conversion is 90.0% for 1HPO and 11.7% for 3HPO, respectively.

From this reaction mixture, the unreacted portion (775.1 g; purity, 99.7%) of cymene is removed by distillation at 70° C. under a pressure of 20 mmHg to give 115.2 g of the concentrate (composition: cymene, 24.8%; 3HPO, 51.7%; 1HPO, 0.96%; CAL, 10.3%; CUL, 6.8%; CUA, 3.9%; CLF, 0.07%; and others, 1.5%).

III. Concentrated sulfuric acid (0.092 g) and acetone (14 g) are placed in a flask, and the mixture is heated to reflux, to which the concentrate (115.2 g) obtained in Sec. II. of this Example is added dropwise under reflux. The reaction mixture is maintained at 65° C. for 0.5 hours. After completion of the reaction, 129.2 g of the solution of decomposition products is obtained (composition: cymene, 22.4%; 3HPO, not found; 1HPO, not found; CAL, 0.57%; CUL, 5.1%; CUA, 3.4%; DMST, 5.6%; CLF, 29.9%; acetone, 27.0%; and others, 6.1%). The yield of cresol from consumed cymene is 60.7%.

IV. In an autoclave made of stainless steel, placed are the solution of decomposition products (129.2 g) obtained in Sec. III. of this Example and 5% palladium carbon catalyst (1.29 g). The reaction is conducted, while introducing hydrogen gas thereinto under a hydrogen gauge pressure of 3 kg/cm$^2$, at 100° C. for 2.5 hours. After completion of the reaction, the catalyst is removed by filtration, and the resulting solution is neutralized by addition of aqueous sodium hydroxide until the water layer had pH 7. From the organic layer obtained, acetone is removed by distillation under normal pressure, and the residue is then distilled under reduced pressure to give 31.5 g of cresol and 46.1 g of cymene. The yield of cresol from consumed cymene is 82.2%.

Comparative Example 1

I. In a reaction vessel equipped with a stirrer, an air-blowing tube, a thermometer and a condenser, placed are cymene (813.1 g; content, 99.0%) and a cymene solution (72.2 g; cymene content, 82.0%; 3HPO content, 12.8%; and 1HPO content, 0.44%) containing cymene hydroperoxide. The reaction is conducted, while blowing air thereinto, at 120° C. under normal pressure for 5 hours. The reaction mixture is then washed at 70° C. with 1% aqueous sodium hydroxide (90 g) to give 905.5 g of a hydroperoxide mixture-containing oil phase (composition: cymene, 82.6%; 3HPO, 11.1%; 1HPO, 2.1%; CAL, 1.1%; CUL, 0.23%; CUA, 0.21%; CLF, 0.03%; and others, 2.6%).

From this reaction mixture, the unreacted portion (687.2 g) of cymene is removed by distillation at 60° C. under a pressure of from 10 to 30 mmHg to give 210.7 g of the concentrate (composition: cymene, 31.5%; 3HPO, 47.4%; 1HPO, 9.2%; CAL, 4.6%; CUL, 1.1%; CUA, 0.85%; CLF, 0.07%; others, 5.4%).

II. Concentrated sulfuric acid (0.19 g) and acetone (27 g) are placed in a flask, and the mixture is heated to reflux, to which the concentrate (210.7 g) obtained in Sec. I. of this Example is added dropwise under reflux. The reaction mixture is maintained at 65° C. for 0.5 hours. After completion of the reaction, 237.9 g of the solution of decomposition products is obtained (composition: cymene, 28.3%; 3HPO, not found; 1HPO, 1.20%; CAL, 0.15%; CUL, 1.6%; CUA, 1.3%; DMST, 1.6%; CLF, 26.3%; acetone, 26.1%; and others, 13.4%). The degree of conversion is 100% for 3HPO and 85.3% for 1HPO, respectively. The yield of cresol from consumed cymene is 63.5%.

III. In an autoclave made of stainless steel, placed are the solution of decomposition products (237.9 g) obtained in Sec. II. of this Example and 1% palladium-titania catalyst (4.76 g). The reaction is conducted, while introducing hydrogen gas thereinto under a hydrogen gauge pressure of 5 kg/cm$^2$, at 75° C. for 2 hours. After completion of the reaction, the catalyst is removed by filtration, and the resulting solution is neutralized by addition of aqueous sodium hydroxide until the water layer has pH 7. From the organic layer obtained, acetone is removed by distillation under normal pressure, and the residue is then distilled under reduced pressure to give 61.6 g of cresol and 84.7 g of cymene. The yield of cresol from consumed cymene is 72.8%.

Comparative Example 2

An acetone solution (0.6 ml) having an adjusted sulfuric acid concentration of $3.29 \times 10^{-3}$ g/ml is placed, together with acetone (4.4 ml), in a flask. The mixture is heated to reflux, to which the concentrate (30.0 g; composition: cymene, 31.5%; 3HPO, 47.4%; 1HPO, 9.2%; CAL, 4.6%; CUL, 1.1%; CUA, 0.85%; CLF, 0.07%; and others, 5.4%) obtained in the same manner as described in Sec. I of Comparative Example 1 is added dropwise under reflux. The reaction mixture is maintained at 65° C. for 0.5 hours. After completion of the reaction, 33.9 g of the solution of decomposition products is obtained (composition: cymene, 28.1%; 3HPO, 32.5%; 1HPO, 5.8%; CAL, 3.2%; CUL, 1.3%; CUA, 0.69%; DMST, 1.7%; CLF, 3.4%; acetone, 15.4%; and others, 7.9%). The degree of conversion is 22.5% for 3HPO and 28.7% for 1HPO, respectively.

EXAMPLES 3 to 9

Partial hydrogenation of a hydroperoxide mixture is conducted in the same manner as described in Sec. II. of Example 1, except for the conditions shown in Table 1. The composition of the hydroperoxide mixture used is as follows: cymene, 81.9%; 3HPO, 12.1%; 1HPO, 2.2%; CAL, 1.0%; CUL, 0.23%; CUA, 0.20%; CLF, 0.01%; and others, 2.4%.

The results are shown in Table 1.

TABLE 1

| Example No. | Alkali washing before hydrogenation | Reaction temp. (°C.) | Kind of catalyst | Amount of catalyst (wt %*1) | Reaction time (hr) | 1HPO conv. (%) | 3HPO conv. (%) | 1HPO/3HPO*2 after reaction |
|---|---|---|---|---|---|---|---|---|
| 3 | None | 28 | 1% Pd/C | 0.1 | 1 | 93.9 | 14.5 | 1/77 |
| 4 | None | 70 | 1% Pd/C | 0.2 | 5 | 91.3 | 21.7 | 1/50 |
| 5 | With 1% NaOH | 70 | 1% Pd/C | 0.1 | 1 | 97.0 | 12.2 | 1/161 |
| 6 | With 1% NaOH | 70 | 1% Pd/TiO₂ | 0.1 | 1 | 98.7 | 8.7 | 1/385 |
| 7 | With 1% NaOH | 70 | 1% Pd/alumina-magnesia | 0.1 | 1 | 95.8 | 14.8 | 1/111 |
| 8 | With 1% NaOH | 70 | 1% Pd/silica-magnesia | 0.1 | 1 | 96.1 | 14.1 | 1/120 |
| 9 | With 1% NaOH | 70 | Raney Ni | 0.7 | 1 | 96.4 | 13.5 | 1/132 |

*¹Amounts based on the weight of the solution of oxygenation products.
*²It refers to the weight ratio of 1HPO to 3HPO.

Each of the reaction mixture obtained in these Examples is concentrated and then subjected to the same operations as described in Secs. II. to IV. of Example 1, and cresols are thus obtained in high yield.

What is claimed is:

1. A process for the production of cresols, comprising the steps of:
   (a) conducting oxygenation of cymene with oxygen gas or an oxygen-containing gas without any addition of an alkali, thereby obtaining a solution of oxygenation products containing tertiary and primary hydroperoxides of cymene;
   (b) washing the solution of oxygenation products obtained in step (a) with an aqueous alkali solution at a temperature in the range of from 10° to 95° C., said aqueous alkali solution having a concentration of 0.1 to 2.0 wt %, and the weight ratio of the aqueous alkali solution to the solution of oxygenation products being in the range of from 1/5 to 1/15 (w/w);
   (c) subjecting the solution of oxygenation products obtained in step (b) to hydrogenation at a temperature in the range of from 60° to 100° C. to decrease the content of primary hydroperoxide in such a manner that the weight ratio of primary hydroperoxide to tertiary hydroperoxide is not greater than 1/25 (w/w);
   (d) subjecting the solution treated in step (c) to decomposition in the presence of a catalyst; and
   (e) subjecting the solution treated in step (d) to hydrogenation to obtain cresols.

2. A process according to claim 1, wherein the oxygenation in step (a) is conducted at a temperature in the rage of from 80° to 150° C.

3. A process according to claim 1, wherein the step (b) is conducted at a temperature in the rage of from 60° to 90° C.

4. A process according to claim 1, wherein the hydrogenation in step (c) is conducted with a Pd catalyst or an Ni catalyst.

5. A process according to claim 1, wherein the degree of hydrogenation of tertiary hydroperoxide in step (c) is 30% or less.

6. A process according to claim 1, wherein the decomposition of step (d) is conducted in a temperature range of from 60° to 150° C.

7. A process according to claim 1, wherein the catalyst in step (d) is selected from the group consisting of acidic catalysts, sulfur and metal complex catalysts.

8. A process according to claim 1, wherein the solution treated in step (c) was concentrated and then subjected to decomposition in step (d).

9. A process according to claim 1, wherein the hydrogenation of step (e) is conducted n a temperature range of from 60° to 250° C.

10. A process according to claim 1, wherein the hydrogenation of step (e) is conducted with a Pd catalyst or a Cu—Cr catalyst.

11. A process according to claim 1, wherein the degree of hydrogenation in step (c) is 15% or less.

12. A process according to claim 1, wherein the weight ratio of primary hydroperoxide to tertiary hydroperoxide in step (c) is not greater than 1/100 (w/w).

13. A process according to claim 1, wherein step (d) is carried out in the presence of a catalyst selected from the group consisting of sulfuric acid, hydrochloric acid, perchloric acid, benzenesulfonic acid, p-toluenesulfonic acid, cresolsulfonic acid, chloroacetic acid, silica-alumina, alumina, strongly acidic ion exchange resin, tungstosilicic acid, tungstophosphoric acid, molybdophosphoric acid, and a catalyst of the general formula

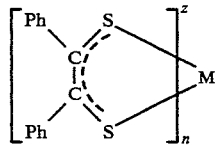

wherein M is Ni, Pd or Fe(II); Ph is a phenyl group which may be optionally substituted with at least one substituent; n is an integer of 1, 2, or 3; and z is a formal charge of the complex, selected from 0, −1 and −2.

14. A process for the production of cresols, comprising the steps of:
   (a) conducting oxygenation of cymene with oxygen gas or an oxygen-containing gas without any addition of an alkali at a temperature of 80° to 150° C., thereby obtaining a solution of oxygenation products containing tertiary and primary hydroperoxides of cymene;
   (b) washing the solution of oxygenation products obtained in step (a) with an aqueous alkali solution at a temperature in the range of from 10° to 95° C., said aqueous alkali solution having a concentration of 0.1 to 2.0 wt %, and the weight ratio of the aqueous alkali solution to the solution of oxygenation products being in the range of from 1/5 to 1/15 (w/w);
   (c) subjecting the solution of oxygenation products obtained in step (b) to hydrogenation at a temperature in the range of from 60° to 100° C. to decrease the content of primary hydroperoxide in such a manner that the weigh ratio of primary hydroperoxide to tertiary hydroperoxide is not greater than 1/25 (w/w);

(d) subjecting the solution treated in step (c) to decomposition in the presence of a catalyst at a temperature of 30° to 150° C.; and (e) subjecting the solution treated in step (d) to hydrogenation at a temperature of 0° to 250° C. to obtain cresols.

15. A process according to claim 14, wherein the step (b) is conducted at a temperature in the range of from 60° to 90° C.

16. A process according to claim 14, wherein the degree of hydrogenation of tertiary hydroperoxide in step (c) is 30% or less.

17. A process according to claim 14, wherein the decomposition of step (d) is conducted in a temperature range of from 60° to 150° C.

18. A process according to claim 14, wherein the hydrogenation of step (e) is conducted in a temperature range of from 60° to 250° C.

19. A process according to claim 14, wherein the weight ratio of primary hydroperoxide to tertiary hydroperoxide in step (c) is not greater than 1/100 (w/w).

* * * * *